US00PP14130P2

(12) United States Plant Patent
Engelke et al.

(10) Patent No.: US PP14,130 P2
(45) Date of Patent: Sep. 2, 2003

(54) ZORRO ZOYSIAGRASS

(75) Inventors: Milton Charles Engelke, Parker, TX (US); James Arnold Reinert, Plano, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/193,356

(22) Filed: Jul. 11, 2002

(51) Int. Cl.[7] ..... A01H 5/00

(52) U.S. Cl. ..... Plt./390
(58) Field of Search ..... Plt./390

*Primary Examiner*—Bruce R. Campell
*Assistant Examiner*—Annette H. Para
(74) *Attorney, Agent, or Firm*—Fulbright & Jaworski L.L.P.

(57) ABSTRACT

The present invention is directed to an asexually reproduced variety of perennial *Zoysia matrella*. The inventive variety demonstrates a unique combination of characteristics including white stigmas, purple-brown anthers, good shade tolerance and turf quality, and resistance to hunting billbug, fall armyworm, yellow patch disease, Rhizoctonia blight and zoysiagrass rust disease.

4 Drawing Sheets

Botanical classification: *Zoysia matrella*.
Variety denomination: 'Zorro'.

BACKGROUND OF THE INVENTION

The invention relates to a new and distinct perennial zoysiagrass cultivar identified as 'Zorro zoysiagrass', referred to herein as 'Zorro'. 'Zorro' is a selection from *Zoysia matrella* plant #124 (unpatented) from a population of 55 experimental clones that were obtained in an exchange for germplasm with the University of Florida, Ft. Lauderdale, Fla. The inventive variety was tested as DALZ8510 and DALZ9601, has been vegetatively propagated and is uniform in growth expression.

In field plot tests evaluated over a 17-yr period at Texas A&M University, Dallas, Tex., 'Zorro' exhibited superior performance as compared to other Zoysia genotypes including commercial cultivars 'Meyer' (unpatented) and 'Emerald' (unpatented). 'Zorro' demonstrates excellent turf quality and shade tolerance, moderate drought tolerance and good defensive traits with resistance to hunting billbug, fall armyworm, yellow patch, Rhizoctonia blight (brown patch) and zoysiagrass rust diseases. The inventive variety is an aggressively spreading *Zoysia matrella* (L.) Merr. that is appropriate for use in the southern United States, particularly in areas that are under either full sun or moderate to heavy shade and employ a mowing height from 1.0 to 5.0 cm. Thus, 'Zorro' is appropriate for use on sports fields, buffer surrounds for bentgrass greens, tee boxes and fairways on golf courses and residential and industrial lawns. Further, 'Zorro' has sufficient winter hardiness that is useful in open areas south of the Missouri River valley and the Appalachian Mountain Range.

For purposes of registration under the "International Convention for the Protection of New Varieties of Plants" (generally known by its French acronym as the UPOV Convention) and noting Section 1612 of the Manual of Plant Examination Procedures, the new variety of zoysiagrass of the present invention is named 'Zorro zoysiagrass'.

BRIEF SUMMARY OF THE INVENTION

The present invention relates to a new and distinct, asexually reproduced, variety of perennial zoysiagrass (*Zoysia matrella* (L.) Merr) between 1 to 3 years of age, so named 'Zorro zoysiagrass'. The inventive variety is characterized by good defensive traits against hunting billbug, fall armyworm, yellow patch, Rhizoctonia blight and zoysiagrass rust diseases among other unique characteristics. These traits are maintained when propagated asexually.

The novel features which are believed to be characteristic of the invention together with further objects and advantages will be better understood from the following description when considered in connection with the accompanying figures.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Characteristics

Figure 1:
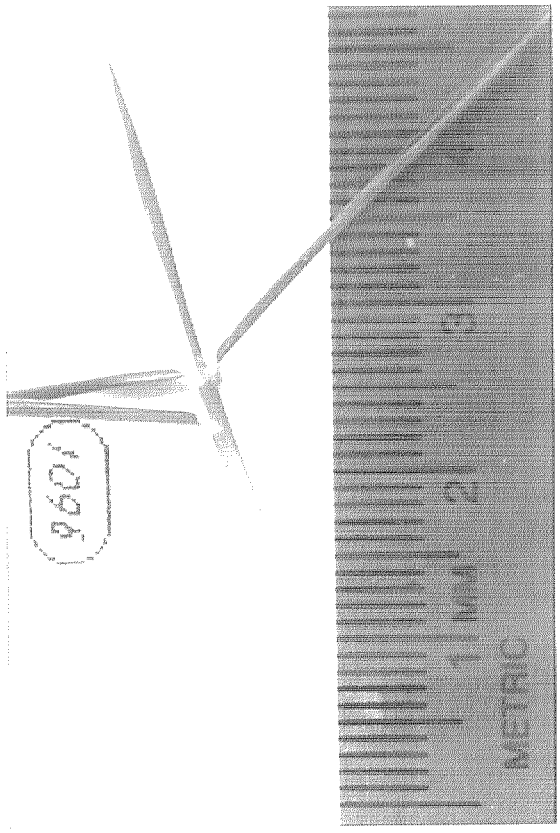
FIG. 1 is a color photograph of the leaf blade and ligule of 'Zorro'.
Figure 2A:
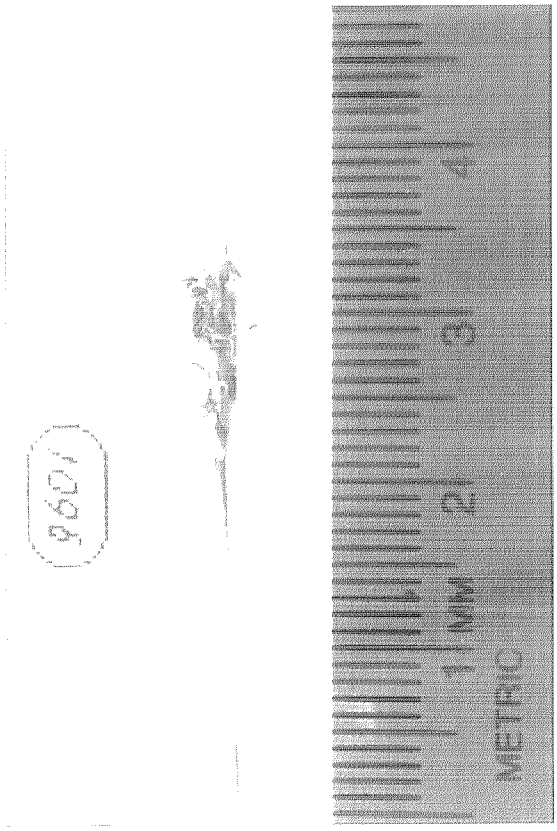
FIGS. 2A and 2B are color photographs of the inflorescence of 'Zorro' in two different magnifications.
Figure 2B:
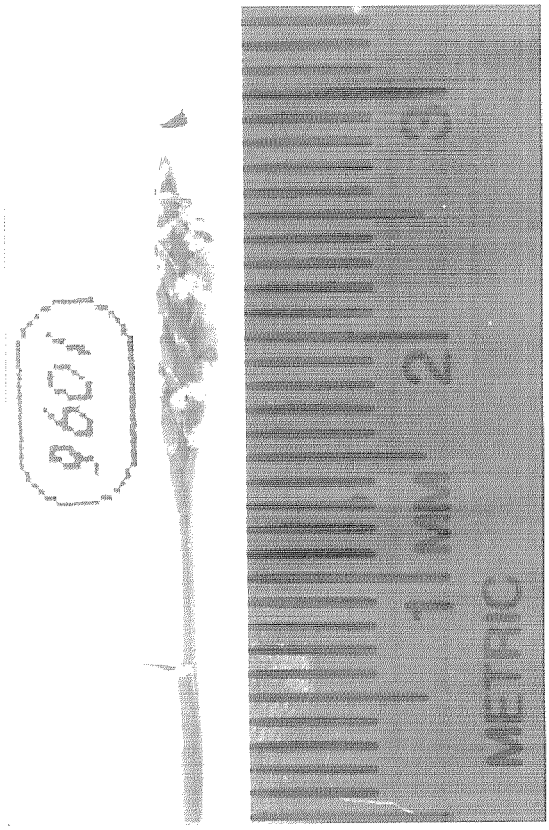

'Zorro' is a unique variety of zoysiagrass that was characterized in cultivation under greenhouse and field conditions. The original selection from plant #124 was vegetatively propagated and expanded in the greenhouse for field testing. Field testing was initially performed in small turf plots. 'Zorro' was identified as a superior genotype and, consequently, was vegetatively propagated by both stolon and rhizome cuttings to provide planting stock for performance studies and for measuring morphological characteristics. 'Zorro' has been propagated by sod, plugs, sprigs, and stolons. Since Zoysia spp. are highly heterozygous, seed propagation by self-pollination is not commonly used and is not recommended because segregation results in a loss of genetic uniqueness and in a difference in the expected performance. No seedling establishment has been observed from plants of 'Zorro' in either the greenhouse or in field plantings.

'Zorro' is distinguished from other varieties of zoysiagrass by a combination of characteristics, including turf quality, shade tolerance, and resistance to hunting billbug, fall armyworm, yellow patch, Rhizoctonia blight and zoysiagrass rust disease. 'Zorro' is closest in phenotypic appearance to the zoysiagrass variety 'Emerald'. It has an intermediate to rapid growth rate, and an intermediate water use requirement. 'Zorro' produces little thatch at an optimum mowing height of 1 to 5 cm. Further, planting 7.5 cm×10 cm plugs of 'Zorro' on 30.5 cm centers or by sprigging provides coverage of a planting area in 10–12 months.

'Zorro' produces both rhizome and stolon growth. The stolons have a mean internode length of 27.0 mm between the fourth and fifth nodes, with a mean internode diameter of 1.25 mm and a node diameter of 1.76 mm (Tables 1) (Reinert et al., 2002a). Also, stolons of 'Zorro' root adventitiously at each node. The internode stolon color for 'Zorro' under full sun is 5GY 7/4.

Color notations of plant tissues were based on the Munsell Color Charts for Plant Tissues, Munsell Color, Baltimore, Md., 1977. One of ordinary skill in the art is aware that color notations are affected by light quality, photoperiod and general growth of the plants. Measured in full-sun under field conditions in August 2000, the genetic, adaxial leaf color of 'Zorro' is 2.5 G 5/2 as compared to 'El Toro', which has a leaf color of 2.5G 4/2 to 2.5 G 5/2, and 'Meyer', which has a leaf color of 2.5 G 4/2, under these conditions.

Leaf blades are rolled in the bud, and are flat and stiff. The leaf blade length is 10.9 mm, which is shorter than 'Meyer' (unpatented) and about the same length as 'El Toro' (U.S. Plant Pat. No. 5,845), and the width is 1.35 mm, which is significantly narrower than either 'Meyer' or 'El Toro' (Table 2). Sparse hairs (trichomes) are present on both the abaxial and adaxial leaf surfaces. The ligule is a row of silky hairs that are characterized by a maximum length of approximately 3 mm.

'Zorro' has a mean flag leaf length of 2.3 mm (as measured under greenhouse conditions, October 2000, Dallas, Tex.). Anthers are purplish-brown, 10 R 5/6, with anthocyanin pigment and stigmas are white and undistinguishable in shade of color (Munsell, 1977). 'Zorro' has a mean culm length of 26 mm, an inflorescence length of 15.3 mm and a mean of 15 florets per raceme.

The somatic chromosome number of 'Zorro' is 40.

'Zorro' exhibits good shade tolerance as compared to the 24 other zoysiagrasses evaluated in the National Turfgrass Evaluation Program, National Zoysiagrass Test-1991 (NTEP-1991). The 25 zoysiagrass varieties were planted and evaluated in a shaded site (ca. 90%) under live-oaks (*Quercus virginiana*) in Dallas, Tex. in September, 1992 (Yamamoto and Engelke, 1996). Turf performance characteristics, including turf quality, turf cover, green cover, color, density and texture were visually evaluated. Turf cover was evaluated as a percentage of plot area covered with turf, and the Turf Performance Index (TPI) was used to evaluate overall turf quality. The TPI is based on the number of times an entry occurred in the top statistical group.

In general, the entries took nearly 9 months to spread and cover at least 50% of the plot area. Thereafter, 'Diamond' (U.S. Plant Pat. No. 10,636) and 'Zorro' increased turf cover to 93.9 and 83.7%, respectively (Table 3). 'Zorro' ranked fourth behind 'Diamond' among the 25 entries, thereby indicating the relatively superior shade tolerance exhibited by 'Zorro'.

Considerable differences in morphological appearance are observed among the zoysiagrasses because, in part, the species classification appears to transcend the textural classes identified by other researchers. Although the appropriate species classification for many of the zoysiagrasses appears under question, White et al. (1993) grouped the grasses into four textural classes based on leaf length and width: (1) short narrow, (2) short wide, (3) long narrow, and (4) long wide leaf types.

*Z. matrella* is generally considered to have a rather narrow leaf blade and, thus, includes plants in classes 1 and 3, whereas, *Z. japonica* has considerably broader leaves and includes plants in classes 2 and 4. The leaf width of a zoysiagrass has also been correlated with water use efficiency. Wide leaf types generally require less water than narrow leaf types, regardless of the length, yet considerable genetic variability occurs. 'Zorro' is a textural class 3 having long narrow leaves, and it has moderate water use requirements, as determined by the Linear Gradient Irrigation System at Dallas, Tex. (Table 4). Over a 3-yr period, 'Zorro' required an average 390 mm of supplemental water. For comparison, 'Emerald' required an average of 437 mm of supplemental water. In the National Turfgrass Evaluation Program, National Zoysiagrass Test-1996 (NTEP-1996) trial at Columbia, Mo. in 1998, 'Zorro' and 'Emerald' both had moderate drought tolerance ratings of 4.7 (Table 5) (Morris, 1998).

In the NTEP-1996 trials, which were evaluated over 4 years (1997–2000), 'Zorro' and 'Emerald' (each given quality ratings of 6.4) topped the list of 19 cultivars that were evaluated at 17 different geographic locations in 15 states of the United States 'Zorro' ranked first for three years, tying with 'El Toro' in 1997 and second to 'Emerald' in 1998. However, the inventive variety was ranked higher than either 'El Toro' or 'Emerald' the last two years of testing (Table 6) (Morris, 1997; Morris, 1998; Morris, 1999; Morris, 2000; and Morris, 2001).

Resistance

'Zorro' exhibited resistance to the hunting billbug (*Sphenophorus venatut vestitus* (Chittenden)) in a cage study with eight other zoysiagrasses at Dallas, Tex. (Table 7) (Reinert et al., 2002b). Compared to 'Meyer' and 'Palisades' (U.S. Plant Pat. No. 11,515) which exhibited 44.4 and 45.5% leaf-firing damage of the plant canopy, respectively, 'Zorro' expressed only 9.8% leaf-firing damage. Evaluation of whole plant growth potential (dry weight) indicated that the inventive variety sustained a 35.7% reduction compared to a 70.2, 73.9 and 73.9% reduction for 'El Toro', 'Meyer' and 'Palisades', respectively, thereby indicating that 'Zorro' sustained less damage and, therefore, expressed greater tolerance to the pest.

'Zorro' exhibited antibiosis (high mortality, slowed growth, and reduced feeding) in lab experiments, thereby indicating resistance to fall armyworm (*Spodoptera frugiperda* J. E. Smith) (Table 8). About 75.0% of the larvae feeding on 'Zorro' were dead before pupation and about 79.2% died before adult emergence. By comparison, 'Diamond' and DALZ8516 produced 16.7% mortality before adult emergence (Reinert and Engelke, 2002). Larvae required a significantly longer development period before pupation (5 days) or emergence of the adults (8 days) on 'Zorro' as compared to susceptible cultivars.

In the NTEP-1996 test evaluated at Riverside, Calif. in 1999, 'Zorro' and 'Emerald', which is a commercial standard, each were rated 9 (on a scale of 1–9 in which 9 indicates no disease) with respect to yellow patch disease, thereby indicating that each are resistant to yellow patch disease (Table 9) (Morris, 1999). Yellow patch disease is caused by the fungal pathogen *Rhizoctonia cerealis* Van der Hoever. Another commercial standard, 'Meyer', was rated 8, but several of the other cultivars in the NTEP-1996 test were susceptible and expressed severe symptoms to yellow patch disease, including 'Korean Common' (unpatented) (rated 6.7), 'Miyako' (U.S. Plant Pat. No. 10,187) (rated 6.7), 'Z-18' (unpatented) (rated 6.0) and 'J-14' (unpatented) (rated 5.7).

'Zorro', 'Emerald' and 'Zeon' are resistant to Rhizoctonia blight (brown patch), which is caused by the fungal pathogen *Rhizoctonia solani* Kühn. Each was rated a 9, using the same scale of 1–9 as described for the yellow patch disease, and showed no symptoms in the NTEP-1996 test evaluation in Griffin, Ga. in 2000 (Table 10) (Morris, 2000). 'Meyer' also demonstrated resistance with a rating of 8, but five other cultivars rated 6.3 or below, including 'Zenith' which was given a rating of 5.0. The resistance in 'Zorro' is supported by an in vitro evaluation of 22 zoysiagrass genotypes in Dallas, Tex. in 2001 (Table 11) (Colbaugh and Engelke, 2002). 'Zorro' was rated 0.23 on a scale of 0–3, in which 0 indicates no disease. In contrast, 'Meyer' and 'Palisades' were rated 1.98 and 2.22, respectively, and expressed significant symptoms of disease.

All of the vegetatively propagated cultivars evaluated in the NTEP-1996 trial at Virginia Beach, Va. in 1997, including 'Zorro', displayed resistance (rating of 9) to zoysiagrass rust, which is caused by *Puccinia zoysiae* Diet. (Table 12) (Morris, 1997). The ratings followed the scale of 1–9, in which a rating of 9 indicates no disease. However, the seeded varieties, as a group, were not resistant and many of them scored quite low. 'Chinese Common' (rated 1.7), 'Zen-500' (rated 2.0) and 'Zenith' (rated 3.0) rated the lowest with the most rust disease symptoms.

Methodology in AFLP for Fingerprint Analysis

Traditionally morphological markers such as plant height, flower color, leaf length, shape and the like were used to identify cultivars. However, many cultivars have similar morphology and are difficult to differentiate. Alternatively, molecular markers have been used widely and successfully for genotyping varieties and species. Amplified Fragment Length Polymorphism (AFLP) is one such highly informative marker assay to generate fingerprints of simple and complex species and cultivars.

Figure 3:
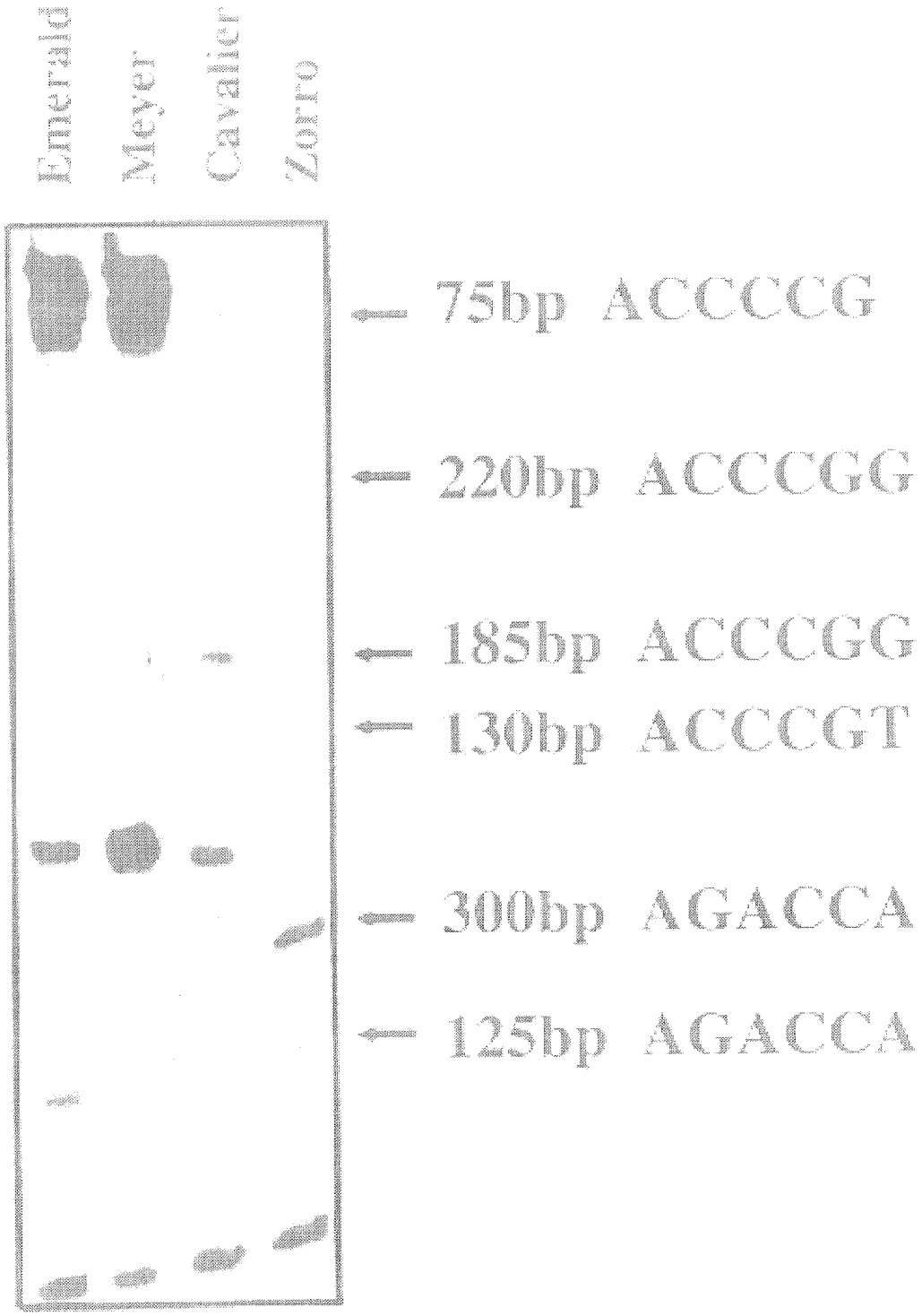
FIG. 3 is a DNA fingerprint of 'Zorro' as compared to zoysiagrass varieties 'Emerald', 'Meyer' and 'Cavalier'.

AFLP was used to generate fingerprints of 'Zorro', 'Emerald', 'Meyer' and 'Cavalier'. The resulting gel analysis is shown in FIG. 3. Of the sixty primer combinations used, the primer combinations P-ACC/M-CCG, P-ACC/M-CGG, P-ACC/M-CGT, P-AGA/M-CCA and P-AGA/M-CCA produced bands unique to 'Zorro', which aid in identification as compared to the other genotypes.

TABLE 1

Rhizome internode length as measured between the fourth and fifth nodes, internode diameter of the fourth internode, and node diameter of the fourth node of nine Zoysia cultivars. Plants grown in sand beds in the field under irrigation during the summer from June to September 2000, Dallas, TX.

| Cultivar | Internode length (mm) | Internode diameter (mm) | Node diameter (mm) |
|---|---|---|---|
| El Toro | 43.6 a[1] | 1.71 a | 2.63 a |
| Palisades | 40.0 ab | 1.55 ab | 2.48 a |
| De Anza | 34.5 bc | 1.39 bc | 1.93 cd |
| Crowne | 31.7 cd | 1.56 ab | 2.36 ab |
| Cavalier | 28.8 cd | 1.38 bc | 1.88 cd |
| Zorro | 27.0 cd | 1.25 c | 1.76 de |
| Meyer | 26.5 cde | 1.54 ab | 2.16 bc |
| Royal | 23.6 de | 1.21 c | 1.53 e |
| Diamond | 18.4 e | 1.19 c | 1.56 e |
| LSD | 8.1 | 0.22 | 0.31 |

[1]Mean in a column followed by the same letter(s) are not significantly different by Fisher's protected LSD (P = 0.01).
Data taken from Reinert et al., 2002a.

TABLE 2

Leaf blade width and length measured on the third youngest leaf of nine Zoysia cultivars. Plants were grown in sand beds in the field under irrigation during the summer from June to September 2000, Dallas, TX.

| Cultivar | Blade width (mm) | Blade length (mm) |
|---|---|---|
| El Toro | 3.51 ab[1] | 10.8 abc |
| Palisades | 3.16 b | 8.5 bcd |
| De Anza | 1.73 c | 6.7 de |
| Crowne | 3.46 ab | 11.1 ab |
| Cavalier | 1.58 c | 10.0 abc |
| Zorro | 1.35 cd | 10.9 ab |
| Meyer | 3.54 a | 12.2 a |
| Royal | 1.36 cd | 8.2 cd |
| Diamond | 1.09 d | 4.4 e |
| LSD | 0.39 | 2.7 |

[1]Mean in a column followed by the same letter(s) are not significantly different by Fisher's protected LSD (P = 0.01).
Data taken from Reinert et al., 2002a.

TABLE 3

Turf performance index and percent cover for the National Turfgrass Evaluation Program; National Zoysiagrass Test-1991 planted under 90% shade at Dallas, TX (1992–1995).

| Entry | TPI[1] | % Plot Cover | Rank |
|---|---|---|---|
| Diamond | 46 | 93.9 | 1 |
| DALZ8516 | 46 | 93.9 | 1 |
| DALZ8508 | 42 | 85.7 | 3 |
| Zorro[2] | 41 | 83.7 | 4 |
| Crowne | 40 | 81.6 | 5 |
| Royal | 40 | 81.6 | 5 |
| 'Emerald | 40 | 81.6 | 5 |
| TC2033 | 40 | 81.6 | 5 |
| Palisades | 38 | 77.6 | 9 |
| Cavalier | 36 | 73.5 | 10 |
| El Toro | 32 | 65.0 | 11 |
| DALZ8701 | 29 | 59.1 | 12 |
| CD2013 | 25 | 51.0 | 13 |
| TGS-W10[3] | 25 | 51.0 | 13 |
| DALZ8501 | 24 | 49.0 | 15 |
| Sunburst | 23 | 46.9 | 16 |
| TC5018 | 22 | 44.9 | 17 |
| ITR90-3 | 19 | 38.8 | 18 |
| K. Common[3] | 17 | 34.7 | 19 |

TABLE 3-continued

Turf performance index and percent cover for the National Turfgrass Evaluation Program; National Zoysiagrass Test-1991 planted under 90% shade at Dallas, TX (1992–1995).

| Entry | TPI[1] | % Plot Cover | Rank |
|---|---|---|---|
| Belair | 16 | 32.6 | 21 |
| Meyer | 16 | 32.6 | 21 |
| TGS-B10[3] | 16 | 32.6 | 21 |
| QT2047 | 15 | 30.6 | 23 |
| JZ-1#A89[3] | 13 | 26.5 | 24 |
| CD259-13 | 11 | 22.4 | 25 |
| QT2004 | 10 | 20.4 | 26 |

[1]TPI = Performance Index is the frequency of occurrence in the top statistical group or when a variety is not statistically different from the top performing variety. Maximum number of observations = 49.
[2]Evaluated as DALZ8510.
[3]Seeded entry.
Data taken from Yamamoto and Engelke, 1996.

TABLE 4

Supplemental irrigation water requirement for commercial and experimental zoysiagrasses during July 1989 through August 1991 on a Linear Gradient Irrigation System at Dallas, TX (1989–1991).

| | Textural | Irrigation requirement (mm) | | | |
|---|---|---|---|---|---|
| Cultivar | Class | 1989 | 1990 | 1991 | Mean |
| Diamond | 1 | 461 | 435 | 567 | 488 |
| DALZ8501 | 1 | 449 | 544 | 429 | 474 |
| FC13521 | 3 | 482 | 448 | 443 | 457 |
| DALZ8517 | 3 | 475 | 402 | 487 | 455 |
| Emerald | 3 | 464 | 343 | 503 | 437 |
| DALZ8506 | 3 | 458 | 379 | 455 | 431 |
| DALZ8515 | 3 | 469 | 419 | 394 | 427 |
| DALZ8508 | 2 | 447 | 379 | 398 | 408 |
| Zorro[3] | 3 | 449 | 310 | 413 | 390 |
| Cashmere | 1 | 435 | 424 | 311 | 390 |
| Cavalier | 3 | 464 | 175 | 441 | 360 |
| DALZ8504 | 2 | 478 | 363 | 138 | 326 |
| DALZ8503 | 2 | 441 | 280 | 193 | 305 |
| DALZ8511 | 2 | 451 | 353 | 200 | 304 |
| DALZ8516 | 2 | 462 | 377 | 25 | 288 |
| Meyer | 2 | 450 | 321 | 74 | 276 |
| Korean Common | 4 | 470 | 174 | 88 | 244 |
| El Toro | 4 | 417 | 21 | 6 | 148 |
| Palisades | 4 | 358 | 26 | 12 | 132 |
| Crowne | 4 | 256 | 12 | 12 | 93 |
| | MSD[1] | 129 | 169 | 242 | 155 |
| | Rainfall[2] | 1092 | 1118 | 1143 | 1118 |

[1]MSD, minimum significant difference for comparison of means within columns based on the Waller-Duncan k-ratio t-test (k = 100) (P = 0.05).
[2]Total annual precipitation.
[3]Tested as DALZ8510 in this experiment.
Data from White et al., 1993.

TABLE 5

Drought tolerance (wilting) ratings of zoysiagrass cultivars from the National Turfgrass Evaluation Program, National Zoysiagrass Test-1996, Columbia, MO (1998).
Drought tolerance (wilting) ratings, 1–9; 9 = no wilting

| Cultivar | Rating[1] |
|---|---|
| El Toro | 7.3 |
| Jamur | 6.3 |
| Miyako | 6.0 |
| Zorro | 4.7 |
| Emerald | 4.7 |

TABLE 5-continued

Drought tolerance (wilting) ratings of zoysiagrass cultivars from the National Turfgrass Evaluation Program, National Zoysiagrass Test-1996, Columbia, MO (1998).
Drought tolerance (wilting) ratings, 1–9; 9 = no wilting

| Cultivar | Rating[1] |
|---|---|
| Meyer | 4.3 |
| Zeon | 4.3 |
| Chinese Common | 4.0 |
| J-14 | 3.7 |
| J-36 | 3.7 |
| J-37 | 3.7 |
| Victoria | 3.7 |
| Zen-500 | 3.7 |
| De Anza | 3.3 |
| Zen-400 | 3.3 |
| Zenith | 3.3 |
| Korean Common | 2.3 |
| HT-210 | 2.0 |
| Z-18 | 2.0 |
| LSD Value[2] | 1.8 |
| C.V. (%)[3] | 28.6 |

[1]Irrigation practice was to prevent stress.
[2]To determine statistical differences among entries subtract one entry's mean from another entry's mean. Statistical differences occur when this value is larger than the corresponding LSD value (P = 0.05).
[3]C.V. (Coefficient of Variation) indicates the percent variation of the mean in each column.
Data taken from Morris, 1998.

TABLE 6

Mean turfgrass quality ratings of zoysiagrass cultivars grown in the National Turfgrass Evaluation Program, National Zoysiagrass Test-1996 at 16 locations in the United States (1997p14 2000).

| | Turfgrass quality ratings 1–9; 9 = ideal turf | | | | |
|---|---|---|---|---|---|
| Cultivar | Overall mean 1997 | Overall mean 1998 | Overall mean 1999 | Overall mean 2000 | 4-yr mean |
| Zorro | 5.8 | 6.5 | 6.8 | 6.8 | 6.4 |
| Emerald | 5.6 | 6.8 | 6.7 | 6.7 | 6.4 |
| Zeon | 5.5 | 6.5 | 6.6 | 6.5 | 6.2 |
| El Toro | 5.8 | 6.4 | 6.1 | 6.1 | 6.1 |
| Jamur | 5.6 | 6.1 | 6.0 | 6.0 | 6.0 |
| Victoria | 5.1 | 6.1 | 5.9 | 5.6 | 5.6 |
| J-14 | 5.5 | 5.7 | 5.6 | 5.4 | 5.6 |
| De Anza | 5.4 | 5.9 | 5.7 | 5.5 | 5.5 |
| Zen-400 | 5.5 | 5.6 | 5.3 | 5.4 | 5.5 |
| J-37 | 5.7 | 5.6 | 5.3 | 5.3 | 5.5 |
| Meyer | 5.0 | 5.6 | 5.5 | 5.6 | 5.4 |
| Miyako | 5.3 | 5.4 | 5.5 | 5.3 | 5.4 |
| Zenith | 5.5 | 5.4 | 5.1 | 5.2 | 5.3 |
| J-36 | 5.4 | 5.4 | 5.3 | 5.2 | 5.3 |
| Zen-500 | 5.2 | 5.3 | 5.2 | 5.1 | 5.2 |
| HT-210 | 5.3 | 5.7 | 5.3 | 4.9 | 5.1 |
| Chinese Com. | 5.4 | 5.2 | 4.9 | 4.9 | 5.1 |
| Korean Com. | 3.2 | 4.4 | 4.6 | 4.6 | 4.2 |
| Z-18 | 3.8 | 3.7 | 4.5 | 4.2 | 4.0 |
| LSD Value[1] | 0.3 | 0.2 | 0.2 | 0.3 | 0.2 |
| C.V. (%)[2] | 16.6 | 9.7 | 9.8 | 11.4 | 19.8 |

[1]To determine statistical differences among entries subtract one entry's mean from another entry's mean. Statistical differences occur when this value is larger than the corresponding LSD value (P = 0.05).
[2]C.V. (Coefficient of Variation) indicates the percent variation of the mean in each column.
Data taken from Morris, 1997; Morris, 1998; Morris, 1999; Morris, 2000; and Morris, 2001.

TABLE 7

Resistance among zoysiagrass cultivars to larval feeding by the hunting billbug, Dallas, TX (June–September 2000).

| Cultivar | Species[1] | Plant response: Plant canopy damage % leaf-firing[2] | Plant response: Total plant mass % reduction[3] |
|---|---|---|---|
| Diamond | Zm | 6.08 a[4] | 26.29 a |
| Zorro | Zm | 9.76 ab | 35.72 ab |
| Cavalier | Zm | 27.58 bc | 48.89 bc |
| Royal | Zm | 20.95 abc | 53.46 cd |
| Crowne | Zj | 40.55 cd | 65.42 de |
| De Anza | Zj | 21.90 abc | 68.64 de |
| El Toro | Zj | 24.93 abc | 70.24 e |
| Meyer | Z | 44.38 d | 73.90 e |
| Palisades | Zj | 45.49 d | 76.10 e |

[1]Zm = *Zoysia matrella*; Zj = *Z. japonica*.
[2]Leaf-firing was considered as an above ground symptom expression of the root feeding damage by billbug larvae. Plants were ranked on a scale of 1–9, 1 = severe leaf firing, 9 = no leaf firing. The % damage = [(check − treatment)/check] × 100.
[3]% reduction for cultivar = [(amount in check) − (amount in treatment)/check] × 100.
[4]Means in a column not followed by the same letter are significantly different by LSD test (P < 0.05).
Data from Reinert et al., 2002b.

TABLE 8

Resistance among Zoysia genotypes (mortality of life stages, weight of larvae and days to pupation and adult emergence) of 4-day-old larvae of fall armyworm fed in a laboratory no-choice study, Dallas, TX (2001).

| Cultivar | Growth responses of fall armyworm larvae: 12-day mortality % | Pupa mortality % | Adult mortality % | 12-day larvae wt (mg) | Days to pupation | Days to adult |
|---|---|---|---|---|---|---|
| Zorro | 75.00 a | 75.00 a | 79.17 a | 43.35 a | 23.33 b | 35.00 b |
| Cavalier | 54.17 a | 58.33 a | 58.33 a | 38.45 a | 25.40 a | 36.00 a |
| Diamond | 16.67 b | 16.67 b | 16.67 b | 180.15 b | 17.80 c | 28.50 c |
| DALZ8516 | 8.33 b | 8.33 b | 16.67 b | 325.07 c | 15.50 d | 25.90 d |

[1]Mean % larvae mortality at days after egg hatch, % mortality at pupation and % mortality at adult emergence (larvae 4-days old when put on grass).
[2]Mean weight of surviving larvae at 12 days after egg hatch (8 days feeding) on each genotype.
[3]Mean number of days from egg hatch to pupation and adult emergence for larvae on genotypes.
[4]Analysis was made on arcsine transformation of the percent mortality: Percent mortality is presented.
[5]Means in a column not followed by the same letter are significantly different by LSD test (P < 0.05).
Data taken from Reinert and Engelke, 2002.

TABLE 9

Yellow patch[1] ratings of zoysiagrass cultivars from the National Turfgrass Evaluation Program, National Zoysiagrass Test-1996 test at Riverside, CA (1999).
Yellow Patch ratings 1–9; 9 = no disease.

| Cultivar | Rating |
|---|---|
| Zorro | 9.0 |
| Emerald | 9.0 |
| Victoria | 9.0 |
| Zen-500 | 9.0 |
| Zeon | 9.0 |
| HT-210 | 8.7 |
| De Anza | 8.3 |
| Jamur | 8.0 |
| Meyer | 8.0 |
| Zenith | 8.0 |
| El Toro | 7.7 |
| Zen-400 | 7.7 |
| Chinese Common | 7.3 |
| J-37 | 7.0 |

TABLE 9-continued

Yellow patch[1] ratings of zoysiagrass cultivars from the National Turfgrass Evaluation Program, National Zoysiagrass Test-1996 test at Riverside, CA (1999).
Yellow Patch ratings 1–9; 9 = no disease.

| Cultivar | Rating |
|---|---|
| Korean Common | 6.7 |
| Miyako | 6.7 |
| Z-18 | 6.0 |
| J-14 | 5.7 |
| LSD Value[2] | 1.5 |
| C.V. (%)[3] | 11.6 |

[1]Yellow patch disease is caused by the fungal pathogen *Rhizoctonia cerealis*.
[2]To determine statistical differences among entries, subtract one entry's mean from another entry's mean. Statistical differences occur when this value is larger than the corresponding LSD value (P = 0.05).
[3]C.V. (Coefficient of Variation) indicates the percent variation of the mean in each column.
Data taken from Morris, 1999.

TABLE 10

Rhizoctonia blight disease[1] ratings of zoysiagrass cultivars from the National Turfgrass Evaluation Program, National Zoysiagrass Test-1996 test at Griffin, GA (2000).
Rhizoctonia blight ratings 1–9; 9 = no disease.

| Cultivar | Rating |
|---|---|
| Zorro | 9.0 |
| Emerald | 9.0 |
| El Toro | 8.7 |
| Jamur | 8.0 |
| Zeon | 9.0 |
| Miyako | 8.0 |
| De Anza | 7.3 |
| J-14 | 6.0 |
| Korean Common | 7.7 |
| Chinese Common | 7.0 |
| J-37 | 7.3 |
| Zen-400 | 7.7 |
| Z-18 | 6.3 |
| Victoria | 7.7 |
| Meyer | 8.0 |
| Zen-500 | 5.3 |
| J-36 | 8.0 |
| Zenith | 5.0 |
| HT-210 | 5.7 |
| LSD Value[2] | 2.0 |
| C.V. (%)[3] | 17.0 |

[1]Rhizoctonia blight disease is caused by the fungal pathogen *Rhizoctonia solani*.
[2]To determine statistical differences among entries, subtract one entry's mean from another entry's mean. Statistical differences occur when this value is larger than the corresponding LSD value (P = 0.05).
[3]C.V. (Coefficient of Variation) indicates the percent variation of the mean in each column.
Data taken from Morris, 2000.

TABLE 11

Rhizoctonia blight disease[1] resistance in an in vitro evaluation of 22 zoysiagrass genotypes, including the 19 cultivars from the National Turfgrass Evaluation Program, National Zoysiagrass Test-1996, Dallas, TX (2001).
Blight ratings: 0–3; 0 = no disease, 3 = heavy disease or death.

| Cultivar | Rating |
|---|---|
| Zorro | 0.23 i[2] |
| Zen-400 | 0.67 hi |
| Zeon | 0.71 g–i |
| Cavalier | 0.73 f–i |

TABLE 11-continued

Rhizoctonia blight disease[1] resistance in an in vitro evaluation of 22 zoysiagrass genotypes, including the 19 cultivars from the National Turfgrass Evaluation Program, National Zoysiagrass Test-1996, Dallas, TX (2001).
Blight ratings: 0–3; 0 = no disease, 3 = heavy disease or death.

| Cultivar | Rating |
|---|---|
| Emerald | 0.78 f–i |
| J-14 | 0.84 e–i |
| Crowne | 1.00 d–h |
| Chinese Common | 1.04 d–h |
| J-36 | 1.16 d–h |
| Victoria | 1.22 d–h |
| HT-210 | 1.23 d–h |
| Zen-500 | 1.24 c–h |
| De Anza | 1.36 b–g |
| Zenith | 1.36 b–g |
| Jamur | 1.42 b–g |
| Z-18 | 1.43 b–f |
| J-37 | 1.44 b–e |
| El Toro | 1.58 a–d |
| Korean Common | 1.58 a–d |
| Miyako | 1.93 a–c |
| Meyer | 1.98 ab |
| Palisades | 2.22 a |

[1]Rhizoctonia blight disease is caused by the fungal pathogen *Rhizoctonia solani*.
[2]Means followed by the same letter are not significantly different by Waller-Duncan k-ratio t test (k = 100) (P = 0.05).
Data taken from Colbaugh and Engelke, 2002.

TABLE 12

Zoysiagrass rust ratings[1] of zoysiagrass cultivars from the National Turfgrass Evaluation Program, National Zoysiagrass Test-1996 at Virginia Beach, VA (1997).
Zoysiagrass rust ratings 1–9; 9 = no disease.

| Variety | Rating[3] |
|---|---|
| Zorro | 9.0 |
| De Anza | 9.0 |
| El Toro | 9.0 |
| Emerald | 9.0 |
| HT-210 | 9.0 |
| Jamur | 9.0 |
| Korean Common | 9.0 |
| Meyer | 9.0 |
| Miyako | 9.0 |
| Victoria | 9.0 |
| Zeon | 9.0 |
| Z-18 | 8.7 |
| J-14 | 8.0 |
| Zen-400 | 4.7 |
| J-36 | 4.3 |
| J-37 | 4.0 |
| Zenith | 3.0 |
| Zen-500 | 2.0 |
| Chinese Common | 1.7 |
| LSD Value[2] | 0.7 |
| CV (%)[3] | 5.9 |

[1]Zoysiagrass rust is caused by *Puccinia zoysiae*.
[2]To determine statistical differences among entries, subtract one entry's mean from another entry's mean. Statistical differences occur when this value is larger than the corresponding LSD value (P = 0.05).
[3]C.V. (Coefficient of Variation) indicates the percent variation of mean in each column.
Data taken from Morris, 1997.

As one of ordinary skill in the art will readily appreciate from the disclosure of the present composition of matter may be utilized according to the present invention. Accordingly, the appended claim is intended to include within its scope such compositions.

REFERENCES

Patents

U.S. Plant Pat. No. 5,845

U.S. Plant Pat. No. 10,187

U.S. Plant Pat. No. 10,636

U.S. Plant Pat. No. 10,778

U.S. Plant Pat. No. 11,570

U.S. Plant Pat. No. 11,515

Publications

Colbaugh, P. F. and M. C. Engelke. 2002. Zoysiagrass susceptibility to *Rhizoctonia solani* Kuhn. (unpublished manuscript).

Morris, K. 1997. National zoysiagrass test—1996, Progress report 1997. Nat. Turfgrass Eval. Prog. U.S. Dep. Agric., Beltsville, Md. NTEP No. 98-4: 87 p.

Morris, K. 1998. National zoysiagrass test—1996, Progress report 1998. Nat. Turfgrass Eval. Prog. U.S. Dep. Agric., Beltsville, Md. NTEP No. 99-5: 82 p.

Morris, K. 1999. National zoysiagrass test—1996, Progress report 1999. Nat. Turfgrass Eval. Prog. U.S. Dep. Agric., Beltsville, Md. NTEP No. 00-6: 82 p.

Morris, K. 2000. National zoysiagrass test—1996, Progress report 2000. Nat. Turfgrass Eval. Prog. U.S. Dep. Agric., Beltsville, Md. NTEP No. 01-16: 92 p.

Morris, K. 2001. National zoysiagrass test—1996, Final Report 1997–2000. Nat. Turfgrass Eval. Prog. U.S. Dep. Agric., Beltsville, Md. NTEP No. 01-15: 129 p.

Munsell Color Service. 1977. Munsell Color Charts for plant tissue. Macbeth Division of Kollmorgen Instruments Corporation, Baltimore Md.

Reinert, J. A. and M. C. Engelke. 2002. Resistance to fall armyworm, *Spodoptera frugiperda*, in zoysiagrass, Zoysia spp. Cultivars. (unpublished manuscript).

Reinert, J. A., M. C. Engelke, J. E. McCoy, D. L. Hays, D. Genovesi and J. J. Heitholt. 2002a. Growth characteristics of nine Zoysia cultivars. (unpublished manuscript).

Reinert, J. A., M. C. Engelke, J. E. McCoy, D. L. Hays and J. J. Heitholt. 2002b. Resistance in zoysiagrass (*Zoysia matrella*) to the hunting billbug (*Sphenophorous venatus vestitus*). (unpublished manuscript).

White, R. H., M. C. Engelke, S. J. Morton and B. A. Ruemmele. 1993. Irrigation water requirement of zoysiagrass, Int. Turfgrass Soc. Res. J. 7: 587–593.

Yamamoto, I. and M. C. Engelke. 1996. 1996 update of zoysiagrass performance fewer than 90% shade conditions. TX Turfgrass Res.-1996. Consolidated Prog. Rep. TURF-96-11: 65–72.

What is claimed is:

1. A new and distinct cultivar of an asexually reproduced *Zoysia matrella* plant, as herein illustrated and described.

* * * * *